United States Patent [19]

Guttman

[11] 4,413,993
[45] Nov. 8, 1983

[54] INFILTRATION-PROOF INTRAVENOUS NEEDLE

[76] Inventor: Yolan R. Guttman, P.O. Box 304, Radio City Station, Bronx, N.Y. 10019

[21] Appl. No.: 314,686

[22] Filed: Oct. 26, 1981

Related U.S. Application Data

[63] Continuation-in-part of Ser. No. 236,105, Feb. 19, 1981, abandoned, which is a continuation of Ser. No. 172,238, Jul. 25, 1980, abandoned, which is a continuation-in-part of Ser. No. 896,340, Apr. 14, 1978, abandoned, which is a continuation of Ser. No. 697,043, Jun. 17, 1976, abandoned, which is a continuation of Ser. No. 602,733, Aug. 7, 1975, abandoned, which is a continuation of Ser. No. 384,081, Jul. 30, 1973, abandoned, which is a continuation-in-part of Ser. No. 156,017, Jun. 23, 1971, abandoned, which is a continuation-in-part of Ser. No. 830,211, Apr. 7, 1969, abandoned, which is a continuation-in-part of Ser. No. 393,688, Sep. 1, 1964, abandoned, which is a continuation-in-part of Ser. No. 313,362, Oct. 2, 1963, abandoned.

[51] Int. Cl.³ .............................................. A61M 5/32
[52] U.S. Cl. .................................................. 604/274
[58] Field of Search .................. 128/214 R, 221, 347; 604/272–274, 117

[56] References Cited

U.S. PATENT DOCUMENTS

| | | | |
|---|---|---|---|
| 2,634,726 | 4/1953 | Nanson | 128/221 |
| 2,862,495 | 11/1958 | Gewecke | 128/221 |
| 3,064,648 | 11/1962 | Bujan | 128/214 R |
| 3,076,457 | 2/1963 | Copen | 128/221 |
| 3,099,988 | 8/1963 | Ginsburg | 128/221 |
| 3,181,336 | 5/1965 | Schofield | 128/221 X |

FOREIGN PATENT DOCUMENTS

| | | | |
|---|---|---|---|
| 446818 | 7/1923 | Fed. Rep. of Germany | 128/221 |
| 1142769 | 4/1957 | France | 128/221 |
| 1196601 | 5/1959 | France | 128/221 |

*Primary Examiner*—Dalton L. Truluck

[57] ABSTRACT

A needle for intravenous injections having a round piercing point lying on the axis of the needle, developed by a gradual inward tapering of the walls of the needle shaft. The point exhibits a solid circumferential surface for some distance back towards the distal end of the needle and an opening is provided at the end of this surface, on one side of the shaft. The location of the opening avoids infiltration of fluids into the tissues surrounding a vein in the event that the tip of the needle penetrates the wall of the vein from inside out. The shape of the needle point permits venipuncture with minimum site trauma and facilitates healing after therapy.

3 Claims, 13 Drawing Figures

INFILTRATION-PROOF INTRAVENOUS NEEDLE

CROSS-REFERENCE TO RELATED APPLICATIONS

This is a continuation-in-part of co-pending application Ser. No. 236,105 filed Feb. 19, 1981; which in turn was a continuation of co-pending application Ser. No. 172,238 filed July 25, 1980; which in turn was a continuation-in-part of application Ser. No. 896,340 filed Apr. 14, 1978; which in turn was a continuation of application Ser. No. 697,043 filed June 17, 1976; which in turn was a continuation of application Ser. No. 602,733 filed Aug. 7, 1975; which in turn was a continuation of application Ser. No. 384,081 filed July 30, 1973; which in turn was a continuation-in-part of application Ser. No. 156,017 filed June 23, 1971; which in turn was a continuation-in-part of application Ser. No. 830,211, filed Apr. 7, 1969; which in turn was a continuation-in-part of application Ser. No. 393,688 filed Sept. 1, 1964; which in turn was a continuation-in-part of application Ser. No. 313,362, filed Oct. 2, 1963; these applications being now abandoned.

BACKGROUND OF THE INVENTION

1. Field of the Invention

This invention relates to needles used by the medical and veterinary professions for the injection of fluids into the veins of human patients and animals.

2. Description of the Prior Art

Needles are utilized for a plurality of purposes in the medical field. The function, or purpose, for which the needle is employed is an important factor in its design. This is particularly true of needles used for long-term intravenous therapy. Most intravenous administration needles have a hub associated with the shaft of the needle which supports the needle and transmits fluids thereto. The needle is inserted into the vein by holding it initially in a position close to the skin and substantially parallel to the vein, it is then pushed forward, penetrating the skin and entering the lumen to reside within the vein. In contrast, intramuscular or hypodermic needles are used for administering relatively small quantities of fluid (usually quite dilute) into tissue. Hypodermic needles generally have a plunger to force out the medication and they are oriented at approximately 45° to the skin surface for an injection.

Obviously, needles used for intravenal injections must be extremely sharp in order to penetrate tissue and vein walls. At the same time, they must have an opening in order to permit passage of fluid through the needle into the vein. It has always been a difficult problem to provide a sufficiently sharp point on intravenous needles while simultaneously providing openings of sufficient size to permit the administration of blood or other relatively thick fluids. The needles presently used for intravenous administration of fluids have cutting points, formed by a beveled end cut with an opening created at the junction of the beveled edge and the needle bore. Such needles slice or slit the skin and vein wall in order to effect entry. U.S. Pat. Nos. 3,064,648 and 3,099,988 to Bujan and Ginsburg, respectively, and the French Pat. No. 1,142,769 to Viala, disclose examples of such needles.

When bevel cut needles are used for the long-term administration of intravenous fluids, the movements of the patient's recipient extremity and the muscular contractions of the vein itself, often cause the point of the needle to penetrate the wall of the blood vessel from the inside out, depositing fluid into the tissues surrounding the vein involved rather than into its lumen. This causes swelling and pain. This is "infiltration", well-known in the medico-nursing professions, as a concommitant phase of intravenous therapy. When infiltration occurs, the needle must be removed and re-inserted at another site. Not infrequently, re-insertion is repeated several times a day for the same patient, resulting in repeated pain and discomfort; not to mention the extended period following treatment during which the swelling and pain may continue. The expenditure of the medico-nursing personnel's time and the cost of such repetitious re-starting of the therapy represent added expenses to hospital management, which are eventually charged as additional expenses to the patients receiving such therapy.

The intravenous needle of the present invention is designed to improve intravenous therapy by substantially eliminating infiltration and by minimizing local trauma and infection. As described hereinafter, this is achieved by use of a puncturing point as distinguished from a cutting tip, and by provision of a closed tip with a single fluid emission opening disposed a measured distance upstream thereof, as distinguished from an end opening. A number of prior art disclosures have touched in varying ways upon the charactertistics which have here been synergistically combined to achieve previously unattained results.

A tapering point is disclosed in U.S. Pat. No. 3,181,336 granted to Schofield. This needle permits the emission of fluids through a slit formed through and along the entire tip. The design permits cutting of the skin and vein, and carries surface debris into the vein during entry. Furthermore, the closeness of the slit opening to the needle tip permits fluid to flow into surrounding tissue when the vein is pierced from inside out.

The disclosure of U.S. Pat. No. 2,634,726 granted to Hanson, bears interesting similarities to the present invention. Its closed tip and single side opening would yield a degree of satisfactory infiltration-proof therapy if other defects were not present. However, the chisel-like bevel cut is imitated, though closed off, and this defeats the goal of a puncture entry as opposed to a cutting entry. This structure also is flawed by placement of the opening on the side of the needle that necessarily rests at the bottom of a vein, because the unsymmetrical point of the needle imposes a specific orientation during insertion.

Finally, one must note the deceptive similarity of structure exhibited between the present invention and several hypodermit needles. The disclosures of U.S. Pat. No. 2,862,495 to Gewecke, French Pat. No. 1,196,601 to Morgun, and German Pat. No. 446818 to Weyl are rather typical of this class of needle. All show emission openings removed from the tip and Morgun even notes the inherent cleanliness of having a solid point rather than an end opening. Nevertheless, each of these needles uses the conical or similar relatively blunt points characteristic and essential for hypodermic injections wherein the needle is used to withdraw fluid from a vial and inject it into tissue as contrasted with long-term intravenous administration into a vein. Such hypodermic needles must have the emission opening relatively near the point to function. As shown by Gewecke and Weyl, hypodermic injections are also more effective if several openings surround the needle at the same location. This too, is completely unsatisfactory for intravenous therapy.

SUMMARY OF THE INVENTION

The present invention provides a needle having a smoothly rounded shaft so that the wound inflicted by the introduction of the needle into the tissue creates a minimum trauma to the tissues involved. The puncture opening effected, permits the surrounding margins of the puncture to completely adhere around the shaft of the needle, thereby preventing the leakage of fluids and the entrance of bacteria and other noxious substances as is the case when needle entry is effected by the slicing or cutting edges of the flattened terminal portion of a needle, such as the beveled tips prevalent today. Healing is also greatly speeded because the rounded puncture point closes substantially completely upon itself when the therapy is terminated and the needle is removed.

In the needle of the present invention, the bore does not extend to its tip; rather, it terminates in an opening that is upstream from the tip by a measured amount. This positioning of the opening insures the infiltration-proof characteristics of the needle since, in the event the tip does penetrate the wall of the blood vessel from the inside, during the course of therapy, the fluid-dispensing opening is still within the lumen of the vein and dispenses the fluid into it rather than into the surrounding tissues.

An object of the invention is to provide an improved intravenous needle that is substantially infiltration proof.

Another object of the invention is to provide an improved intravenous needle which may be more easily inserted into the vein with less pain.

Another object of the invention is to provide an improved intravenous needle which inflicts less injury to the member in which it is inserted and which permits more rapid healing following therapy.

Another object of the invention is to provide an improved intravenous needle that effects entry by puncture rather than by cutting or slicing the skin and veins.

In accordance with the invention, there is provided an intravenous needle for insertion in a vein to supply fluid, comprising a round hollow needle shaft having a sharp point which exhibits a solid circumferential surface extending upstream for a distance equal to at least several diameters of the shaft. The point retains a round cross-section throughout and has the tip lying on the axis of the needle shaft. The tip is developed by a gradual inward tapering of the walls of the shaft commencing with a smooth curve from said walls. An opening on one side of the needle shaft only, at a measured distance upstream from the tip, communicates with the hollow bore of the needle shaft to permit fluid flow into the vein only, even when the point of the needle penetrates beyond the wall of the vein.

The above objects, as well as further objects and advantages of the invention, will be more clearly understood from the following description of the invention which is taken in conjunction with the attached drawings.

DESCRIPTION OF THE PREFERRED EMBODIMENT

Figure 1:
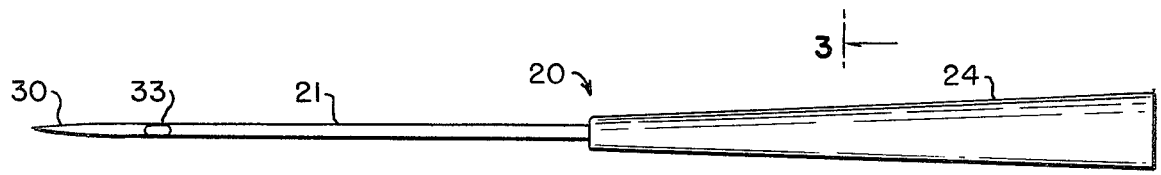
FIG. 1 is a side view of an intravenous needle of the type contemplated by the present invention, mounted in a hub portion.
Figure 2:
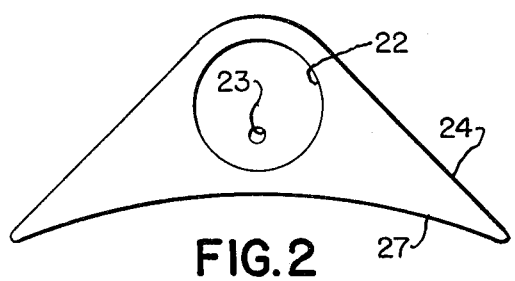
FIG. 2 is an end view from the hub end of the needle illustrated in FIG. 1 illustrating the opening in the hub through which fluid is inserted.

The needle and hub assembly shown in FIG. 1 includes a hollow needle shaft 21 and hub or connecting portion 24. The hub 24 may have a flat, laterally concave lower surface 27 and be of the type shown, for example, in the inventor's U.S. Pat. No. 3,509,880, issued May 5, 1970. As illustrated more clearly in FIG. 2, hub 24 has a flat, rearwardly facing opening 22 formed to accommodate a standard Luer tapered syringe type outlet or any equivalent fitting. Extending forward from the large rearward facing opening 22 is a smaller channel 23 which is positioned to communicate with the rear of hollow needle shaft 21. Hub 24 is rigidly connected to an open end of needle shaft 21.

Figure 3:
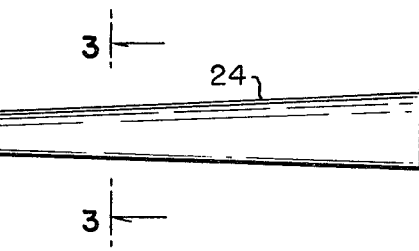
FIG. 3 is a section taken along line 3—3 of FIG. 1, illustrating the channel through the hub which passes fluids to the needle.
Figure 4:
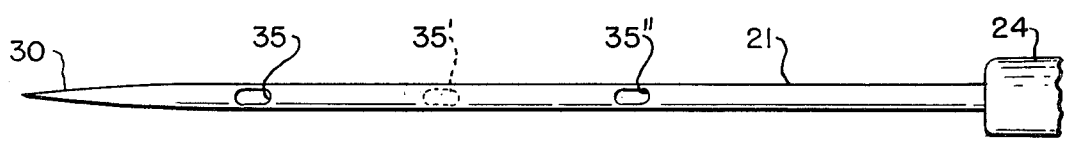
FIGS. 4, 5, and 6 are enlarged side views of the needle illustrating embodiments of the present invention.
Figure 5:
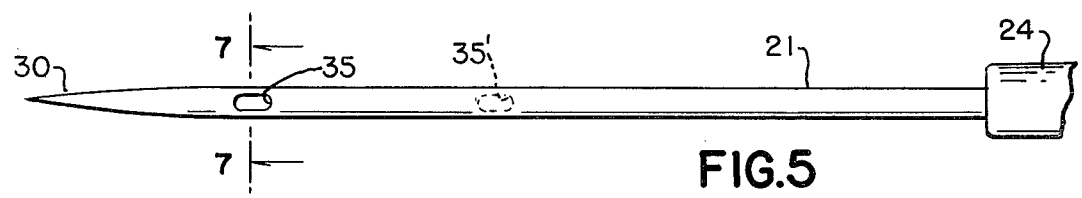
Figure 3A:
FIGS. 3A through 3D illustrate sections through typical hubs that might advantageously be used in combination with needles embodying the features of the invention.
Figure 3B:
Figure 3C:
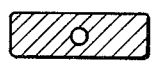
Figure 3D:

FIGS. 3 through 3D show typical cross-sectional shapes which may be used for optimum performance with the needle design of this invention. Still other cross-sections will be apparent to those skilled in the art. While this needle will function in any rotational position, the least preferred position would be to place the opening 33 at the bottom of the vein. Thus, preferably the cross-section of the hub provides a physical indication of the rotational orientation of the needle that is immediately apparent to the user. Furthermore, the portion of the hub or connecting means positioned adjacent to the patient should be designed to prevent inadvertent rolling or other movement. The hub may be provided with a self-adhesive base, or may be secured in position with a bandage or adhesive tape. In some applications, it may be found that a cuff may be used in combination with the needle to hold it in the desired position.

The detailed structure of an intravenous needle embodying the features of this invention will be seen in FIGS. 4 through 7. Needle shaft 21 terminates at its forward end in a tip portion 30. The point of the needle is located upon the axis of the needle shaft 21. As illustrated more clearly in the cross-sectional view of FIG. 7, the needle shaft is circular. This circular configuration extends right to the tip 30 of the needle. The position of the point assists in directing the insertion and its configuration prevents undue trauma during insertion. Still further, the round cross-section of the point causes the least puncture opening and permits most rapid healing upon termination of the therapy. It is important to note that the sides of needle shaft 21 flow in a smooth unbroken curve from the needle wall to tip 30, from a distance of optimum choice at least several times greater than the diameter of shaft 21. This dimensioning provides a gradually tapering, completely rounded piercing point and affords a tip that is sufficiently slender and sharp to easily penetrate the surrounding tissue and wall of the vein. As the needle shaft is advanced into the vein, the opening created by this slender, rounded piercing point is gradually enlarged in diameter, but remains completely rounded, with the tissues around the venepuncture closely adhering to the shaft 21 of the needle. The wall of the vein, being somewhat elastic, thus bears against the shaft 21 of needle 21 and will completely close upon withdrawal of this needle.

Figure 6:
Figure 7:
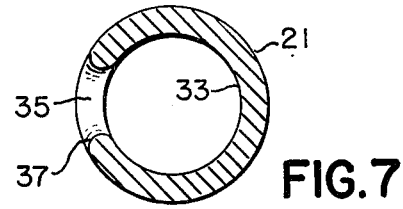
FIG. 7 is a sectional view taken along line 7—7 of FIG. 5 and illustrating the formation of an opening in accordance with an embodiment of the invention.

With specific reference to the embodiment of the invention as shown in FIG. 6, it will be seen that the discharge opening 35 of the needle, is located some distance removed from the tip 30. Such openings may be rounded, oval, angular or slitted. Preferably, the opening 35 is positioned with its leading edge approximately at the point of inception of the inwardly tapering curve. Thus, where this curve begins at a location four diameters removed from the point, the opening 35 will have its leading edge positioned at this location and the entire surface of the needle shaft is closed and smooth downstream thereof. The opening is located back of the piercing point at a sufficient distance to have the opening remain within the blood vessel if the tip of the needle should penetrate the wall of the vessel after venepuncture will have been accomplished and the fluid therapy started. Typical and effective embodiments of the invention utilize needles 1 inch and 1.5 inches in length, with the opening positioned approximately one-third upstream from the tip.

Figure 8:
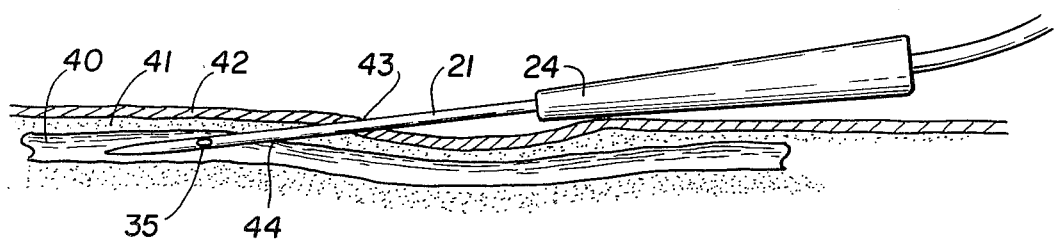
FIG. 8 is a partial vertical sectional view exagerated to show a needle properly inserted in a vein.
Figure 9:
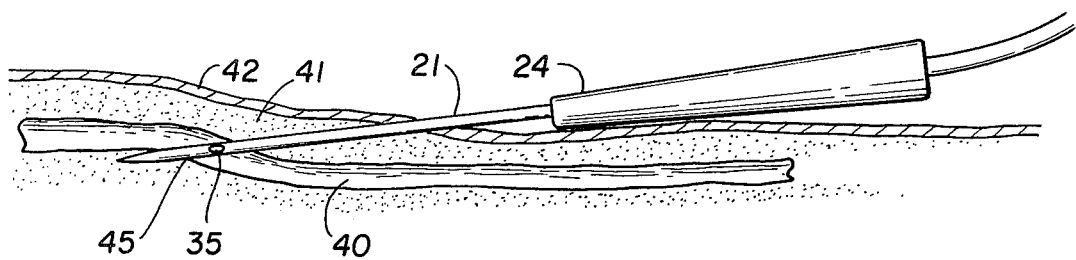
FIG. 9 is a partial vertical sectional view exagerated to show a needle inserted in a vein with the point penetrating into the surrounding tissue.

FIGS. 8 and 9 illustrate the importance of the proper positioning of the opening 35. FIG. 8 shows a properly inserted needle penetrating the skin 42, surrounding tissue 41, and the upper wall of a vein 40. Opening 35 lies within vein 40 and the punctures at 43 and 44 are substantially sealed against the needle shaft because of the fine rounded point of the needle. The fluid being administered will not seep out into the surrounding tissues. It will be noted that the optimum unrestricted flow will take place if the opening 35 is not in direct contact with a vein wall. Thus, advantageously, the needle should be rotationally oriented about its longitudinal axis to place the opening in a direction other than downward. This orientation can best be assured by initial mounting in a connecting means or hub that may be discretely oriented. Such connecting means are discussed in connection with FIGS. 3 through 3D.

FIG. 9 shows why the needle of this invention is substantially infiltration proof. In this exaggerated figure, the tip of the needle has pierced the lower wall of the vein 40, causing a puncture 45. As previously explained, the shape of the needle assures that puncture 45 will seal against the needle wall due to the elasticity of the vein walls. This will prevent escape of fluid from the vein into the surrounding tissue. In addition, because opening 35 is upstream from the tip, it is still within the vein and will continue to supply fluid thereto.

Every extremity has some degree of flexibility. Although the distal end of the needle is securely affixed to the skin of a patient, there is some pivoting of the needle assembly about the point of entry and some longitudinal movement of the needle tip within the vein. The maximum extent of this movement is ascertainable and the opening 35 in the needle must be located back from the tip by at least the amount of this maximum movement. This assures that if the point penetrates the vein wall from the inside, the opening 35 remains within the vein. In addition, the opening must not be so far upstream that it will fall outside the vein. These criteria apply irrespective of the diameter and length of the needle.

In constructing the needle of this invention, one may use either a hollow tube and forge the end into the illustrated form, or one may use separate pieces for the tip and shaft and weld these pieces together. The opening may be contoured to avoid the tearing of skin that occurs when sharp-edged slits are used as orifices. The particular technique of fabrication must in all instances assure that the basic structure of the invention is attained.

It is known that at least three factors are important with respect to the administration of intravenous fluid. These factors are the suction effect of the blood vessel, the patency of the blood vessel, and the external pressure imparted to the fluid (e.g. by gravity feed). The opening should be of size to utilize the suction capacity of the blood vessel, with a needle of appropriate gauge selected the opening shall be of suitable size in keeping with the consistency of the fluid to be administered.

There has been shown and described specific embodiments of the invention and it will be appreciated that modifications in these specific embodiments may be made by those skilled in the art. Modifications coming within the scope and teachings of the description and appended claims, are intended to be covered thereby.

What is claimed is:

1. An intravenous needle for insertion into a vein to supply fluid thereto, said needle preventing infiltration of fluids into tissues surrounding said vein, said intravenous needle comprising a round elongated hollow needle shaft tapering to a completely round elongated tip terminating in a sharp point which exhibits a solid, imperforate circumferential surface, said point retaining a round cross section throughout, said point lying on the axis of the needle shaft and an opening of said needle shaft at a measured distance spaced from said point, said distance being sufficient to permit said opening to remain within the lumen of said vein even when the point of such an inserted needle penetrates the wall of the vein from inside out.

2. An intravenous needle as defined in claim 1, wherein the leading edge of said opening is positioned along the needle shaft from said point of the shaft by a distance equal to several diameters of said shaft.

3. The intravenous needle of claim 1 wherein the opening does not interrupt the smooth surface of the shaft of the needle.

* * * * *